(12) United States Patent
Nissl

(10) Patent No.: US 9,925,076 B2
(45) Date of Patent: Mar. 27, 2018

(54) STENT

(71) Applicant: NOVATECH SA, La Ciotat (FR)

(72) Inventor: Thomas Nissl, OT Adendorf (DE)

(73) Assignee: NOVATECH SA, La Ciotat (FR)

( * ) Notice: Subject to any disclaimer, the term of this patent is extended or adjusted under 35 U.S.C. 154(b) by 23 days.

(21) Appl. No.: 14/786,112

(22) PCT Filed: Apr. 17, 2014

(86) PCT No.: PCT/EP2014/001033
§ 371 (c)(1),
(2) Date: Oct. 21, 2015

(87) PCT Pub. No.: WO2014/173511
PCT Pub. Date: Oct. 30, 2014

(65) Prior Publication Data
US 2016/0143757 A1    May 26, 2016

(30) Foreign Application Priority Data
Apr. 22, 2013   (DE) .......................... 10 2013 104 062

(51) Int. Cl.
*A61F 2/915* (2013.01)
*A61F 2/848* (2013.01)

(52) U.S. Cl.
CPC .............. *A61F 2/915* (2013.01); *A61F 2/848* (2013.01); *A61F 2002/91541* (2013.01);
(Continued)

(58) Field of Classification Search
CPC ................. A61F 2002/91583; A61F 2230/006
See application file for complete search history.

(56) References Cited

U.S. PATENT DOCUMENTS 5,591,197 A  *  1/1997  Orth ......................... A61F 2/07
                                                        606/191
6,033,433 A     3/2000  Ehr et al.
                        (Continued)

FOREIGN PATENT DOCUMENTS

DE      19822157 A1    11/1999
DE      20023387 U1     1/2004
                (Continued)

OTHER PUBLICATIONS

International Search Report issued by the European Patent Office in International Application PCT/EP2014/001033.

*Primary Examiner* — Thomas J Sweet
*Assistant Examiner* — Megan Wolf
(74) *Attorney, Agent, or Firm* — Henry M. Feiereisen, LLC

(57) ABSTRACT

A stent in the form of a generally tubular body has multiple annularly expandable serpentine elements. The serpentine elements have arcs at the first and second element ends which point in the axial direction of the stent. Annularly expandable serpentine elements which follow one another in the axial direction are connected to one another via connectors which are arranged at the ends of the adjacent elements. The connectors extend in the circumferential direction of the stent in the non-expanded state of the stent and have a curvature in the circumferential direction. In the expanded state of the stent, the curvature is so great in the circumferential direction that the connectors project radially outward beyond the circumference of the serpentine elements.

12 Claims, 10 Drawing Sheets

(52) U.S. Cl.
CPC .............. *A61F 2002/91575* (2013.01); *A61F 2002/91583* (2013.01); *A61F 2230/006* (2013.01); *A61F 2250/0039* (2013.01)

(56) References Cited

U.S. PATENT DOCUMENTS

| | | | |
|---|---|---|---|
| 6,273,911 B1 | 8/2001 | Cox et al. | |
| 7,645,297 B2 | 1/2010 | Nissl | |
| 7,691,142 B2 | 4/2010 | Nissl | |
| 2001/0027339 A1* | 10/2001 | Boatman | A61L 31/022 623/1.15 |
| 2002/0151959 A1 | 10/2002 | von Oepen | |
| 2002/0193867 A1* | 12/2002 | Gladdish, Jr. | A61F 2/91 623/1.15 |
| 2003/0139799 A1 | 7/2003 | Ley et al. | |
| 2005/0137688 A1* | 6/2005 | Salahieh | A61F 2/2418 623/2.11 |
| 2005/0149168 A1 | 7/2005 | Gregorich | |
| 2006/0020322 A1 | 1/2006 | Leynov et al. | |
| 2007/0208416 A1 | 9/2007 | Burpee et al. | |
| 2009/0248133 A1* | 10/2009 | Bloom | A61F 2/2418 623/1.15 |
| 2010/0286760 A1* | 11/2010 | Beach | A61F 2/91 623/1.22 |
| 2013/0116774 A1* | 5/2013 | Strauss | A61B 17/12118 623/1.35 |

FOREIGN PATENT DOCUMENTS

| | | |
|---|---|---|
| DE | 29825178 U1 | 11/2005 |
| EP | 1703859 B1 | 4/2011 |
| GB | 2494820 A | 3/2013 |
| WO | WO 03/061528 A1 | 7/2003 |
| WO | WO 2006/022949 A1 | 3/2006 |
| WO | WO 2012/071542 A2 | 5/2012 |

* cited by examiner

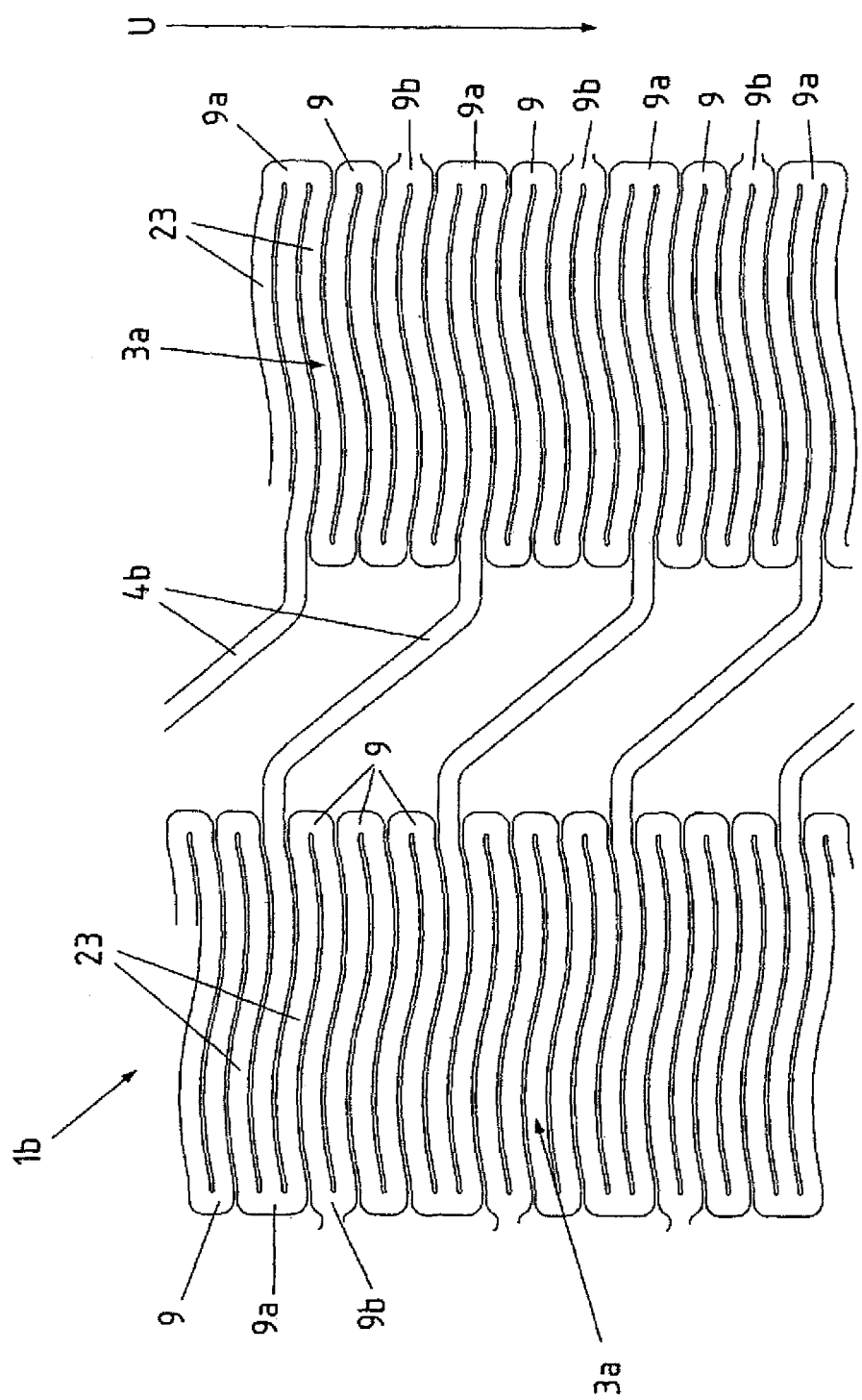

STENT

CROSS-REFERENCES TO RELATED APPLICATIONS

This application is the U.S. National Stage of International Application No. PCT/EP2014/001033, filed Apr. 17, 2014, which designated the United States and has been published as International Publication No. WO 2014/173511 and which claims the priority of German Patent Application, Serial No. 10 2013 104 062.4, filed Apr. 22, 2013, pursuant to 35 U.S.C. 119(a)-(d).

BACKGROUND OF THE INVENTION

The invention relates to a stent in the form of a substantially tubular body, including: multiple serpentine, annularly expandable elements, wherein the serpentine elements have first and second ends facing in axial direction of the stent, wherein the first and second ends have arcs; and Y-shaped connectors connecting axially adjacent ones of the serpentine elements, each of the connectors having a base arm and two fork arms, the base arm being connected to one of the arcs of the second end of one of the adjacent serpentine elements, the two fork arms being connected to two neighboring ones of the arcs of the first end of the other one of the adjacent serpentine elements in one to one correspondence, wherein in a non-expanded state of the stent the connectors extend in circumferential direction of the stent and have a curvature in the circumferential direction, the curvature in an expanded state of the stent having a size in the circumferential direction so that the connectors protrude radially outwardly over a circumference of the serpentine elements.

A stent is a medical implant that is introduced into a hollow organ to hold it open. It is a radially expandable endoprothesis, which is radially enlarged at the target position. Stents can be made of self-expanding materials or can be expanded by radial forces exerted from inside, for example by way of a balloon dilatation. Stents are made of different materials. In most cases they are made of metals such as stainless steel or from memory alloys such as Nitinol.

In the case of stents made of metal, the state of the art includes a design in which the generally tubular body of the stent has multiple serpentine, annularly expandable elements. These serpentine elements have arcs, which point in the axial direction of the stent. The arcs are connected via legs, which point in axial direction. Hereby, serpentine, annularly expandable elements that succeed each other in axial direction are interconnected via so-called connectors, which are usually arranged at the ends of the neighboring elements. Such an arrangement is known from WO 2006/022949 A1. The connectors are configured so as to enable expansion of the serpentine, ring-shaped elements. At the same time the stent is intended to have a smallest possible radius during the transluminal implantation. In WO 2006/022949 it is therefore proposed that the connectors overlap each other in the compressed position.

DE 29 825 178 U1 provides for helical connectors with multiple arms, which lead to the arcs of the neighboring elements. The helical connectors are quasi uncoiled when the stent expands so that the serpentine, annularly expandable elements, which serve the support function of the stent, can expand in radial direction.

GB 2 494 820 A1 discloses a stent for bridging an aneurysm. In the middle region, the stent is to be slightly widenable in order to introduce occlusion material into the neighboring aneurysm. Between serpentine elements, the stent has connectors, which extend in circumferential direction of the stent and have a curvature in circumferential direction of the stent. In an expanded stent, the curvature in circumferential direction is of a size so that the connectors protrude radially outwardly over the circumference of the serpentine element. While the serpentine elements substantially define a cylindrical region, an outwardly oriented bulge results in the middle section in the region of the connectors between the individual connectors. Here, the distance between the connectors is greater than in the region of the serpentine elements, so as to enable introducing occlusion material through this region into the neighboring aneurysm. A narrowing of the distances between the struts would impede the introduction of occlusion material into the aneurysm.

The state-of-the-art also includes WO 03/061528 A1, which relates to a so-called multilayer stent. There are serpentine segments and connectors. The connectors can be strongly bent and protrude outwardly over the cylindrical region of the stent.

DE 200 23 387 U1 discloses a stent with serpentine elements and connectors arranged therebetween. The connectors are configured as straight webs.

However, the connectors can also be curved, as disclosed in US 2007/0208416 A1. The connectors can allow a change of length of the stent.

The connectors known from WO 2012/071542 A2 can, in some exemplary embodiments, be configured Y-shaped. A base arm is connected with an arc at the end of a first serpentine element. The fork arms are Y-shaped, however, they divide once more so as to be respectively connected with three neighboring arcs at the end of the other serpentine, annularly expandable elements.

EP 1 703 859 B1 discloses a stent for placement on a curved region of a body cavity. The stent has serpentine elements and connectors arranged therebetween, which can be straight or curved. The connectors are not fork-shaped or Y-shaped. In contrast thereto DE 198 22 157 A1 proposes a radially expandable stent for implantation in a body vessel, in which branching connectors are provided, which however are additionally twisted in themselves. This is intended to create additional expansion possibilities in order to pass a second non-widened stent through the radial openings or even to radially widen the second stent in the region of the openings. Hereby the cross-sectional surface of the openings in the sheath surface of the stent has to be significantly enlarged. The stent is for example intended for placement in the region of branching points of vessels.

SUMMARY OF THE INVENTION

The invention is based on the object to improve a stent in the form of a generally tubular body with multiple serpentine, annularly expandable elements so that the stent is better secured against axial displacement within the body vessel after the radial expansion of the serpentine elements.

This object is solved with a stent with the features of patent claim 1.

Advantageous refinements of the invention are the subject matter of the dependent claims.

A stent according to the invention in the form of a generally tubular body with multiple serpentine, annularly expandable elements has, as is known, connectors. The connectors are fastened on arcs, which in axial direction of the stent are located at the first and second ends of the respective serpentine, annularly expandable element. The connectors, which in an unexpanded state of the stent extend in circumferential direction of the stent, have a curvature in circumferential direction, wherein in the expanded state of the stent the curvature is of a size in circumferential direction so that the connectors protrude radially outwardly over the circumference of the serpentine element. As a result, in the expanded state of the stent the connectors form ring-shaped, outwardly protruding thickenings, which counteract a displacement of the stent in longitudinal direction of the body cavity.

In the non-expanded state, the stent is intended to have a smallest possible outer diameter to be able to minimally invasively place the stent. The radius of the stent is the reciprocal of the curvature. This curvature of the connectors is substantially retained during the expansion of the stent. Because the remaining sheath surface decreases during the radial expansion of the stent, the curvature of the more strongly curved connectors protrude radially outwardly. They are displaced out of the sheath surface of the serpentine elements.

When the connectors are sufficiently bending stiff, the curvature is theoretically fully retained. In practice, however, the curvature slightly decreases because during expansion of the stent opposing torques act on the ends of the connectors. In this case the curvature is only retained substantially, because the deformation of the radially protruding regions is within the elastic deformation range of the material.

In the starting position, the connectors extend over one third to two thirds of the circumference of the non-expanded stent, i.e., over 120° to 240°. This angle decreases during expansion of the stent relative to the circumference of the stent because the connectors do not increase in length during the expansion of the stent. In the expanded state they extend over a circumference range of 30° to 85°. The circumference ranges covered by the connectors overlap so that the connectors form a radially outwardly protruding wreath.

During the expansion, the serpentine elements adjoining the connectors are rotated relative to each other in opposite directions. This is due to the fact that the connectors do not increase in length while at the same time being displaced outwardly, so that in contrast to the starting position the connectors do not extend over for example 120° of a small cylinder sheath with a diameter of for example 5 mm, but rather over for example 30° of a greater cylinder sheath with a diameter of 20 mm.

The connectors extend quasi helically in the manner of a multi-start thread between the neighboring serpentine elements. The orientation of all connectors following each other in axial direction of the stent can be identical. However, it is advantageous when the connectors on one axial end of the serpentine element extend in opposite direction relative to the connectors on the other axial end of the serpentine element. This enables rotation of neighboring serpentine elements alternately in opposite directions, without rotation of the entire stent. An example: in an arrangement E-K1-E-K2-E, wherein in this sequence E stands for serpentine element and K1 and K2 for connectors extending circumferentially in opposite directions, the end-side elements E can retain their starting position and only the middle element E is rotated in opposite circumferential direction relative to the end-side elements E. The connectors K1 and K2 are thereby spread apart in radial direction. In the case of connectors oriented in the same direction, i.e., in an arrangement E-K1-E-K1-E, the outer elements E would have to be rotated in the same direction but twice as far.

The connectors can be connected to the opposing ends of the serpentine elements. This means that the connectors are connected with the outsides of the arcs of the serpentine elements.

As an alternative it is possible that the connectors are connected with the ends of the serpentine elements that face away from each other, i.e., to the insides of an arc. The connectors extend as far as into the region covered by the serpentine elements. As a result they are suspended somewhat softer because a longer lever is formed up to the fastening point on the inside of a distal arc.

Mixed forms are also possible in which the connector is connected on one side with an outside of an arc and on the other side with an inside of an arc. In the context of this invention, the fact that the connectors are connected with an end of the serpentine element does not necessarily mean that this end is the closest end of the serpentine element. It can also be the other, distal end of the serpentine element, i.e., it can be a connection with the inside of the respective arc.

The connectors have three arms, i.e., are configured Y-shaped. This means that a base arm of the connector is connected with an arc on the end of the first serpentine, annularly expandable element, while the two fork arms of the Y-shaped connector are respectively connected with one of two neighboring arcs on the end of the other serpentine, annularly expandable element.

The Y-shaped connectors, which can also be referred to as divided connectors, are supported by the radial force of the individual serpentine elements. At the same time the flexibility of the stent remains ensured. The connectors can also be arranged next to each other in the compressed starting position, i.e., at a diameter of the stent of for example 5 mm. The connectors do not overlap in radial direction of the stent, so that no thickening occurs in the region of the connectors. Of course there is also no overlap when the stent reaches its final diameter. Such a final diameter can for example be 20 mm. For example the stent is a tracheal stent.

In addition the Y-shaped connectors have the special property that when spreading the fork arms apart, as it is the case during stretching of the stent, the fork arms exert a force on the forking point of the connector. The forking point is the point at which the fork arms are connected with the base arm. The forking point is displaced radially outwardly relative to the cylinder sheath formed by the neighboring elements. This means that in the expanded position the connectors protrude further radially outwardly over the substantially cylindrical stent than the serpentine elements. The connectors exert an outwardly oriented radial force onto the surrounding tissue. This radial force or the radially outwardly protruding connectors result in a better anchoring of the stent in the body cavity and additionally mechanically secure the stent against longitudinal displacement within the body cavity.

According to the invention it is therefore regarded particularly advantageous when multiple of the expandable serpentine elements follow connectors in axial direction of the stent, so that a sequence of connectors and serpentine elements results which functionally complement each other with regard to the outwardly oriented radial force, because each serpentine element is supported on at least one end by a connector. The connectors not only act as connecting member between the serpentine elements, but also as anchoring element for the stent. The more connectors are provided the better the anchoring effect of the stent in the body cavity. Depending on the length of the stent, 3 to 5 or also more connectors can be arranged between a corresponding number of elements following each other in axial direction. The outer appearance of the stent can be compared to a bamboo rod in the expanded state. The node-like thickenings of the bamboo rod correspond to the radially outwardly oriented connectors, while the serpentine, annularly expandable elements correspond to the cylindrical sections therebetween. This geometry is of course only present in the expanded position.

Should it become necessary to remove the stent again, wherein the stent is compressed again in order to revert it to a starting diameter, the connectors are caused to assume their starting position again and no longer protrude in radial direction over the serpentine elements. This also facilitates removal of the stent.

In order to achieve a most uniform anchoring by the outwardly acting connectors, preferably all arcs of a serpentine element are connected with the arcs of the neighboring serpentine element via the connectors. Generally the serpentine elements can also be coupled with each other, when every second, third or fourth arc is provided with a connector. The serpentine element can therefore also have arcs without connected connectors. However, because the connectors do not only function to connect the serpentine elements with each other, but also actively contribute to anchoring the stent, it is sought to maximize the number of connectors.

In a preferred embodiment, the base arm of the Y-shaped connector is curved in a development plane of the stent. As a result the arc of the one element connected with the base arm is located in a different circumferential section than those arcs of the other element with which the fork arms are connected. The curvature of the base arm thus extends within the cylindrical sheath surface of the stent. When viewing the stent as development of a cylindrical sheath surface, the curvature lies in the development plane, which corresponds to the sheath plane of the stent.

The fact that the connecting point of the base arm lies in a different circumferential section than the forking point via which the fork arms adjoin, makes it possible that during widening of the stent the forking point can be displaced radially outwardly out of the circumferential plane. The base arm serves hereby a support function as pivot arm and supports the forking point so that the forking point remains in the pivoted position.

In an advantageous refinement, also the fork arms are curved when viewed in a development plane of the stent so that the forking point, at which the base arm is connected with the two fork arms, lies in a different circumferential section of the stent than those arcs of the annularly expendable elements on which the fork arms are fastened.

The curvature of the fork arms has the same function as the curvature of the base arms: the forking point is intended to be better supported and guided during its radially outward displacement. The required degree of freedom of the forking point is achieved in that the ends on which the fork arms are fastened are displaced relative to each other. The curvature of the fork arms hereby supports a pivoting of the fork arms relative to each other and with this also of the common forking point. The outwardly displaced forking point is thus supported in the expanded position of the stent by three arms, on one side by the base arm and on the other side by the two fork arms. This 3-point-support enables a defined force distribution over the three arms of the connector. The position of the forking points is exactly defined due to the geometry of the fork arms. The position of the forking point can only be displaced by changing the distance of the arcs relative to each other when compressing or expanding the stent. Without this displacement the forking point safely and reliably remains pivoted out in the expanded position of the stent so that long-term fixing of the stent is also ensured via the outwardly oriented connectors.

Tests have shown that it is particularly advantageous when the fork arms, which for establishing the curvature each have a fork arm arc, are differently curved when viewed in a development plane of the stent. The fork arm arcs thus have different radii of curvature. These deviations regarding the radii of curvature lead to the fact that the fork arms, which are connected to each other in the forking points, perform different movements when two neighboring arcs move apart. Depending on the curvature of the fork arm arcs, this movement contributes to displacement of the forking point in a defined direction to a defined degree.

The fork arms can have different lengths. Even though it would be possible to configure the fork arms to have the same length, for example by differently positioned or differently curved fork arm arcs, the desired support of the common forking point particularly advantageously results when the fork arms have different lengths.

In a further embodiment, the fork arms, when viewed in a development plane of the stent, have a first length section, in which the fork arms extend parallel to each other. Already these parallel extending length sections can have different lengths. In other words the different length of the fork arms does not necessarily result from different curvatures of the fork arm arcs.

The connectors, when viewed in a development plane of the stent, preferably have an S-shaped course starting from the arc on which the base arm is fastened, and proceeding in the direction of the arcs on which the fork arms are fastened. This means that the curvatures of the fork arms and those of the base arm are oriented in different directions. The forking point is located outside the curvatures, approximately in the center of the distance between the serpentine elements. When each arm, i.e., the two fork arms and also the base arm, have an arc, the middle regions of the Y-shaped connectors, i.e., also the region in which the forking point is located, is situated approximately diagonally relative to the longitudinal axis of the stent.

Within the framework of the invention it is further provided, that the thickness of the arms of a connector measured in radial direction is greater than the width of the arms measured in circumferential direction. This means that the connectors are constructed relatively delicately, but are sufficiently bending stiff in circumferential direction so as to retain the desired original curvature also in the expanded position. On the other hand, the serpentine elements, which serve for exerting an outwardly directed radial force, are configured in the opposite manner. They preferably have a thickness measured in radial direction, which is smaller than the width measured in circumferential direction. This is due to the fact that the serpentine elements have to exert a high resistance force, especially in the region of the end-side arcs, in order to remain in the expanded position. The arc has to have a sufficient section modulus, which can only be achieved by corresponding cross-sections. On the other hand, the connectors, which for manufacturing reasons are located in the same development plane of the stent as the serpentine elements, undergo torsion when the stent expands, in particular in the Y-shaped variant. In order to avoid impeding the expansion of the stent, the section modulus resisting the torsion must not be excessive. Therefore the connectors are quasi narrower than the serpentine elements, in particular narrower than the arcs. The arcs on the other hand have to absorb the torsion moments of the fork arms and the base arm of the connectors, simultaneously absorb a force which acts from outside on the radially protruding connectors and in addition hold the serpentine elements in the expanded position. Therefore the region of the arcs is subjected to the highest loads and therefore has the greatest cross section.

Within the framework of the invention it is possible to combine different designs of connectors. This means that divided connectors may be formed in a length section and un-divided connectors in another length section.

BRIEF DESCRIPTION OF THE DRAWING

In the following, the invention is explained in more detail by way of the exemplary embodiments schematically shown in the drawings.

It is shown in.

DETAILED DESCRIPTION OF PREFERRED EMBODIMENTS

Figure 1:
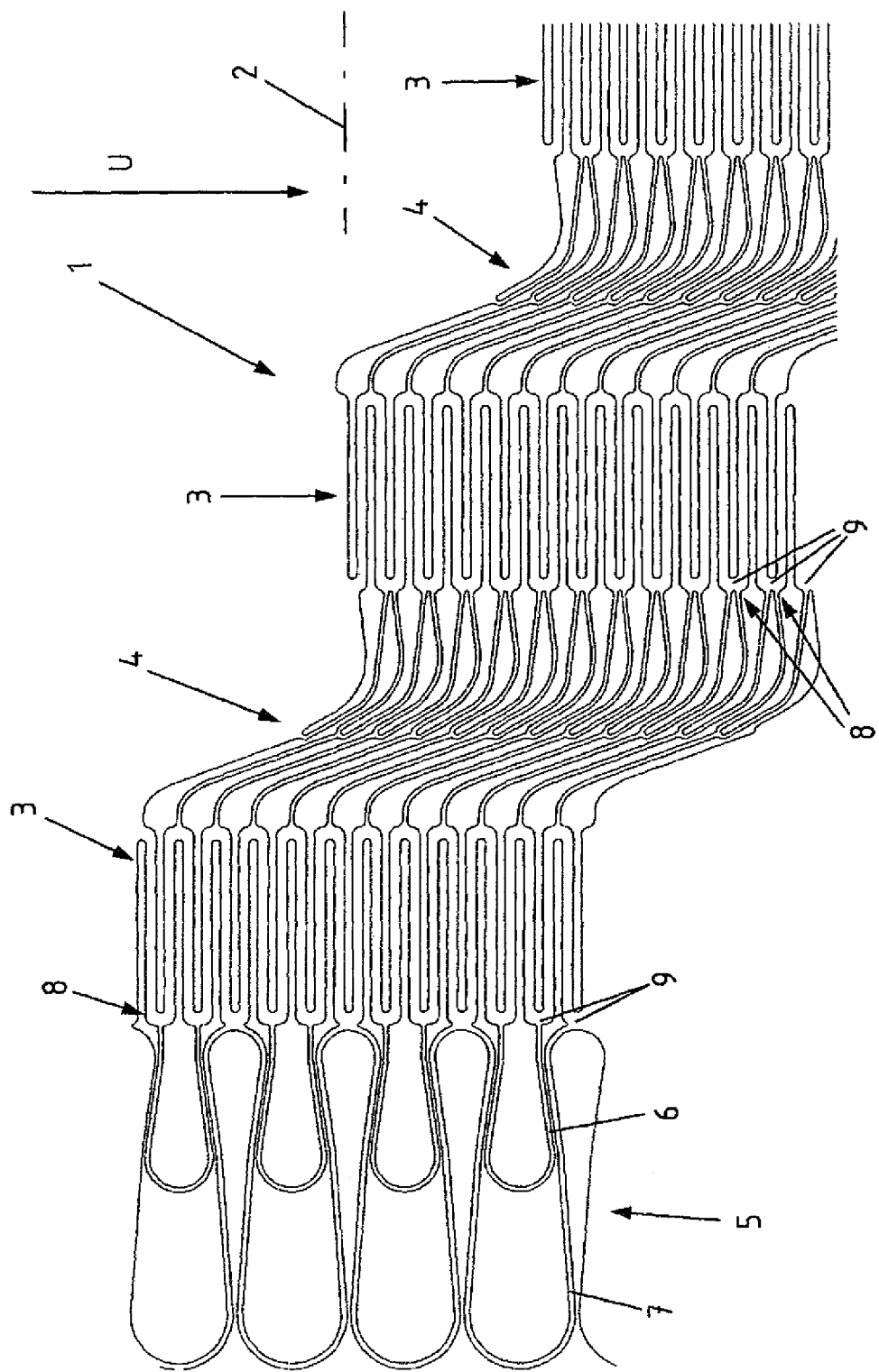
FIG. 1 a view onto a development of the sheath surface of the stent, in the non-expanded state, in a first embodiment.

FIG. 1 shows the development of a stent 1 in a first embodiment. It is the sectional view of a metal component produced by laser cutting. In the cylindrical form this development forms a tubular body, which is formed about the longitudinal axis 2.

The stent 1 having this design substantially has three different functional sections: the most massive components are serpentine, annularly expandable elements 3, which in the image plane of FIG. 1 extend from top to bottom. Within the tubular body the serpentine, annularly expandable elements extend in circumferential direction (arrow U). These elements 3 recur at regular axial distances. The individual elements 3 are interconnected via connectors 4. While the serpentine, annularly expandable element 3 represents only a single circumferentially extending element 3 per radial plane, the elements 3 which neighbor each other in axial direction are interconnected via a plurality of connectors 4.

The stent 1 also has an end section 5. The end section 5 is made of shorter loop-like arcs 6 and, viewed in axial direction, longer arcs 7 surrounding the shorter arcs 6. The shorter arcs 6 are each connected with an end 8 of the serpentine element 3, which is on the left-hand side in the image plane. The arcs 6, 7 of the end section 5 are each connected with the end-side arcs 9 of the serpentine element. As a result, in the end section 5 the greater arcs 7 extend meander-shape in circumferential direction of the stent 1, similar to the serpentine elements 3.

The stent 1 is not shown in its full length. The second end of the stent 1 also has an end section 5 with arcs 6, 7.

Figure 2:
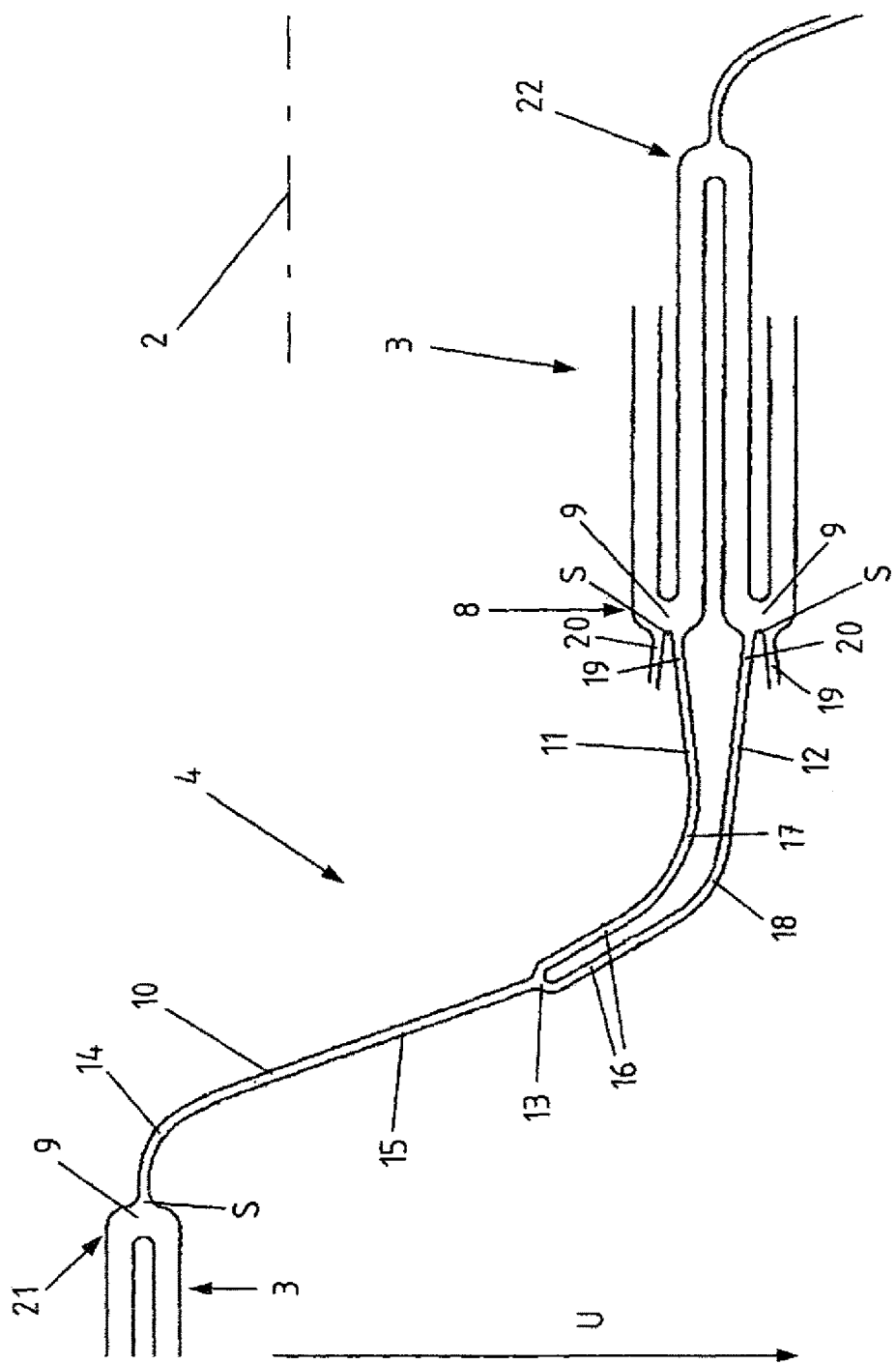
FIG. 2 an enlarged representation of individual connectors in the view shown in FIG. 1.

FIG. 2 shows the construction of the connectors 4 and their connection with the elements 3 in more detail in an enlarged view. The connectors 4 are configured Y-shaped. All connectors 4 are configured identical. They each have a base arm 10 and two fork arms 11, 12. Located approximately midway between the elements 3 is a forking point 13 of the connector 4.

In the apex S of an arc 9, the base arm 10 is connected with this arc 9 on the outer circumference of the arc 9. The base arm 10 branches off from the arc 9 so as to quasi point in the direction of the longitudinal axis 2. In immediate proximity to the arc 9, the base arm 10 is positioned perpendicular to the arc 9. Adjoining in the further course of the base arm 9 is a base arm arc 14. In the image plane of FIG. 2, the base arm 10 thus bends downward in the direction of the forking point 13. In this exemplary embodiment, the connection between the base arm arc 14 and the forking point 13 is straight and represents the main section 15 of the base arm 10. In this exemplary embodiment, the main section 15 extends at an enclosed angle of 70 degrees relative to the longitudinal axis 2. According to the invention the enclosed angle between the main section 15 and the longitudinal axis is within a range of 50° to 75° degrees.

The arrow U again indicates the circumferential direction of the stent. It can be recognized that as a result of the bending of the base arm 10, the forking point 13 is located within a different circumferential region than the arc 9, on which the base arm 10 is fastened. When taking the distance of the apexes S of two arcs 9 as unit of measurement along the circumferential direction, the forking point 13 is further offset in circumferential direction than the arc 9 on which the base arm is fastened by about 4 to 5 apex distances.

In the cylindrical state, i.e., not in the development of the cylinder sheath of the stent, the connector 4 extends over a circumferential section of the non-expanded stent from 120° to 240°. During expansion this angle becomes smaller and is only 30° to 85°. The more the stent is expanded the smaller the circumferential range covered by the connectors 4 becomes and the smaller the overlap of the individual connectors 4 becomes. In the shown developed view the overlap is maximal.

The two fork arms 11, 12 are fastened on neighboring arcs 9 of the element 3 on the right-hand side in the image plane. They are offset relative to the arc 9 on which the base arm is fastened by approximately 5 to 6 apex distances in circumferential direction.

The base arm 10 has a constant width. The fork arms 11, 12 have the same width as the base arm. Starting from the forking point 13, they lead into a first length section 16, in which the two fork arms 11, 12 extend parallel to each other. The length section 16 of the upper fork arm 11 in the image plane is slightly shorter than the corresponding length section 16 of the lower fork arm 12. Adjoining these two length sections, which although extending parallel to each other do not align with the main section 15 of the basic section, is a respective fork arm arc 17, 18 of the respective fork arm 11, 12.

The length section 16 is bent by approximately 5 degrees relative to the orientation of the main section 15. This means that the length sections 16 of the two fork arms 11, 12 are located at an angle of approximately 65 instead of 70 degrees relative to the longitudinal axis 2. The angle between the base arm 10 and the fork arms 11, 12 can be 1-10°.

The fork arm arc 17 of the upper fork arm 11 in the image plane extends over a greater angular range than the other fork arm arc 18. Although the radius of curvature of this first fork arm arc 17 is greater than the radius of curvature of the other fork arm arc, the upper fork section 17 has overall a stronger curvature than the lower fork section 18, in spite of the smaller curvature (curvature=reciprocate of the radius of curvature). As a result the upper fork arm 11 is slightly shorter than the other fork arm 12, which has to extend in circumferential direction U slightly further to the lower one of the two arcs 9 of the element 3 on the right-hand side in the image plane. On the arcs 9 on the first ends 8 two respective fork arm ends 19, 20 of neighboring connectors 4 are fastened. The fork arms 19, 20 are arranged adjacent the apex S of the respective arc 9 and branch off V-shaped adjacent the apex S of the arc 9. Due to the V-shape the fork arms 11, 12 are arranged at a greater distance to each other than in the region of their fork arms 17, 18 or than in the parallel length sections 16. As a result, the fork arms 11, 12 are spread apart quasi V-shaped.

Overall each individual connector 4 extends S-shaped between first ends 21 and second ends 8 of neighboring serpentine, annularly expandable elements 3.

Figure 3:
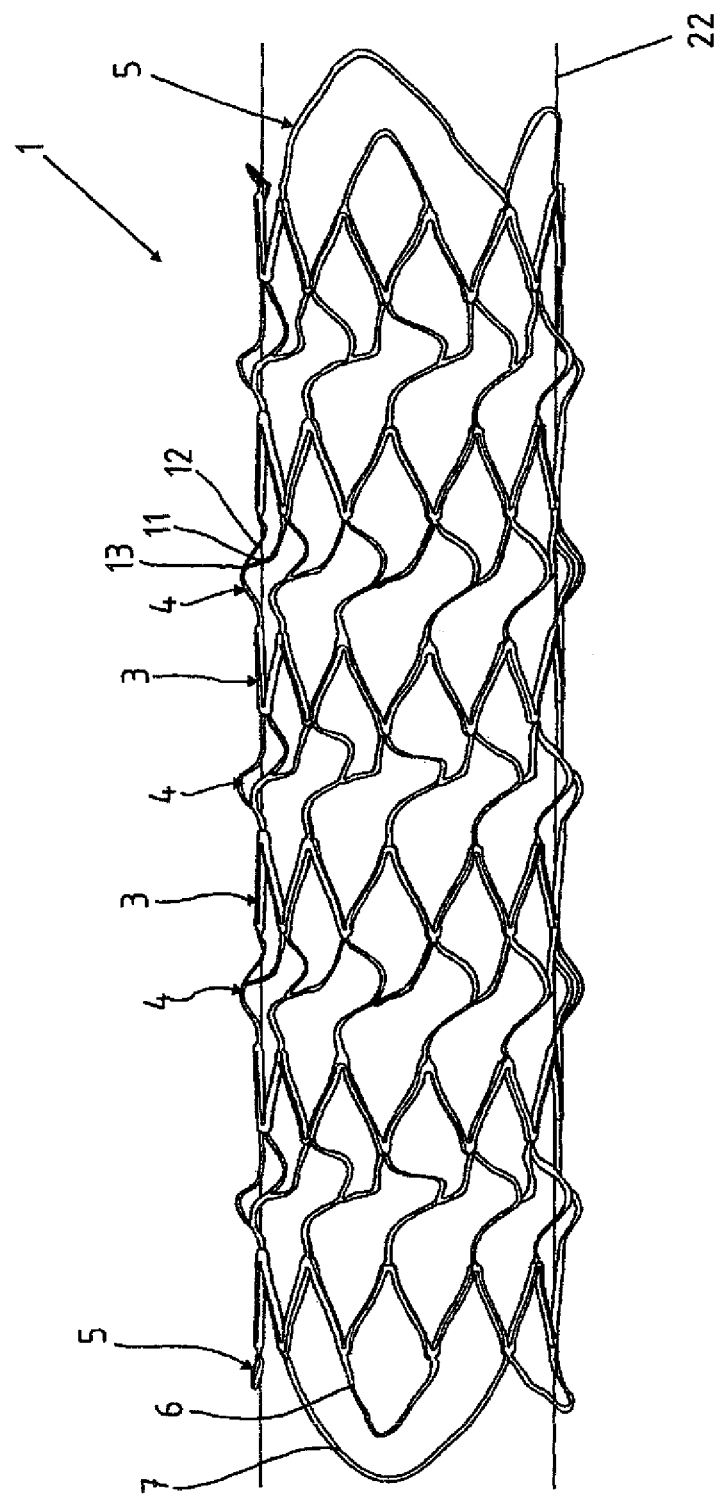
FIG. 3 a perspective view of an expanded stent having the design of FIGS. 1 and 2.
Figure 4:
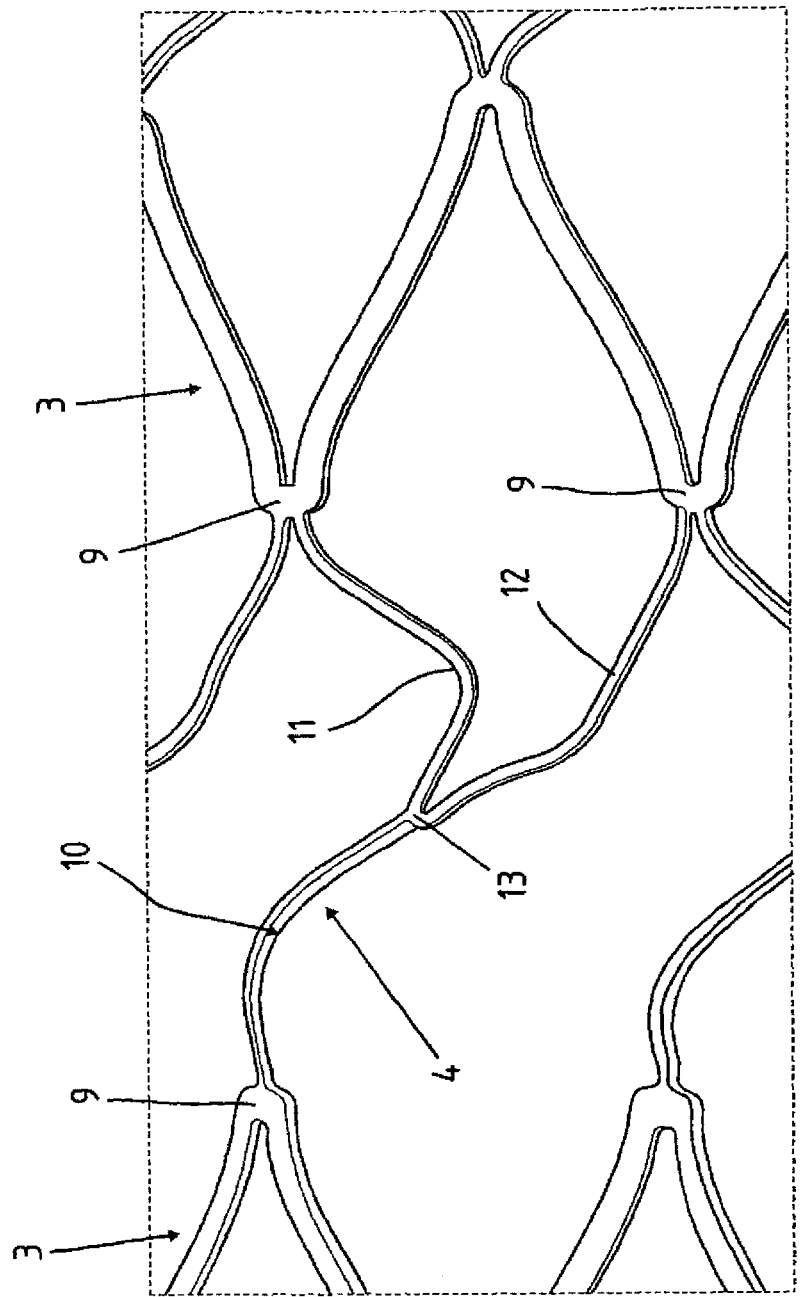
FIG. 4 an enlarged representation of a partial region of FIG. 3.
Figure 5:
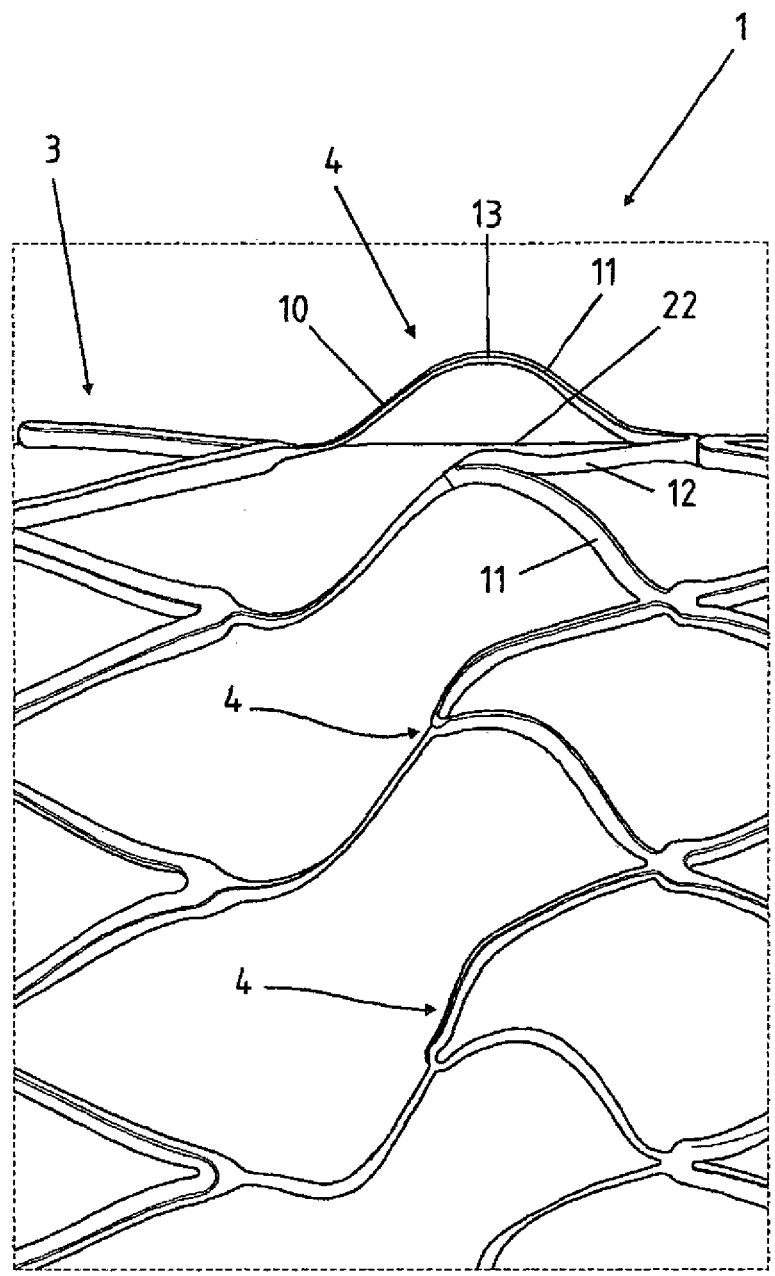
FIG. 5 a further enlarged representation of a partial region of FIG. 3.

While FIGS. 1 and 2 show the stent 1 in a developed view, i.e., in a not yet tubular state and non-expanded state, FIGS. 3 to 5 illustrate the appearance of the stent 1 in the expanded state.

FIG. 3 shows the stent of FIGS. 1 and 2. For better illustration, the stent 1 is arranged on a cylinder 22. The cylinder 22 is meant to illustrate the state of the stent 1 during expansion. After the expansion the cylinder 22 is removed again so that the stent 1 remains in the body cavity and holds the body cavity open.

The stent 1 again has the multiple serpentine, ring-shaped and now expanded elements 3 and the Y-shaped connectors 4 arranged between the elements 3. In addition FIG. 3 shows end sections 5 with the inner and outer arcs 6, 7 in the expanded state.

It can be seen that the connectors 4 significantly protrude upwards and downwards, i.e., in radial direction, over the cylinder 22. They are in the expanded position, i.e., they are no longer located completely in the same cylindrical sheath surface as the serpentine elements 3, which overall tightly rest against the cylinder 23 and quasi form the scaffold for the tubular structure of the stent 1. In the region of the fork arms 11, 12 the connectors 4 are strongly spread apart. The forking point 13 is displaced radially outwardly and is lifted off from the cylinder sheath 22.

The enlarged representation of FIG. 4 shows that the individual fork arms 11, 12 are relatively strongly deformed. A relatively large distance between the arcs 9 of the elements 3 is bridged by the two fork arms 11, 12 as a result of the spreading apart of the serpentine, annularly expandable elements 3. As a result the fork arms 11, 12 are twisted in opposite directions and respectively exert oppositely oriented torques on the forking point 13 of the connector 4. At the same time the base arm 10 engages on the forking point 13 and supports the forking point 13. As a result of the torques exerted by the fork arms 11, 12 the base arm 10 is pivoted relative to the arc 9 on which the base arm 10 is fastened. The middle region of the connector 4 is lifted out of the sheath surface formed by the serpentine elements 3. This is illustrated particularly clearly in FIG. 5. The uppermost connector 4 in the image plane is significantly lifted from the cylinder 22 in its middle region. The connector 4 serves for additional anchoring of the stent 1 in the surrounding tissue (not further shown). The remaining connectors 4 extend in like manner, i.e., the forking points 13 between the fork arms 11, 12 and the base arm 10 are significantly lifted from the cylinder 22 so that overall a circumferential bulge-like elevation of the shown lattice structure of the stent 1 results.

Figure 6:
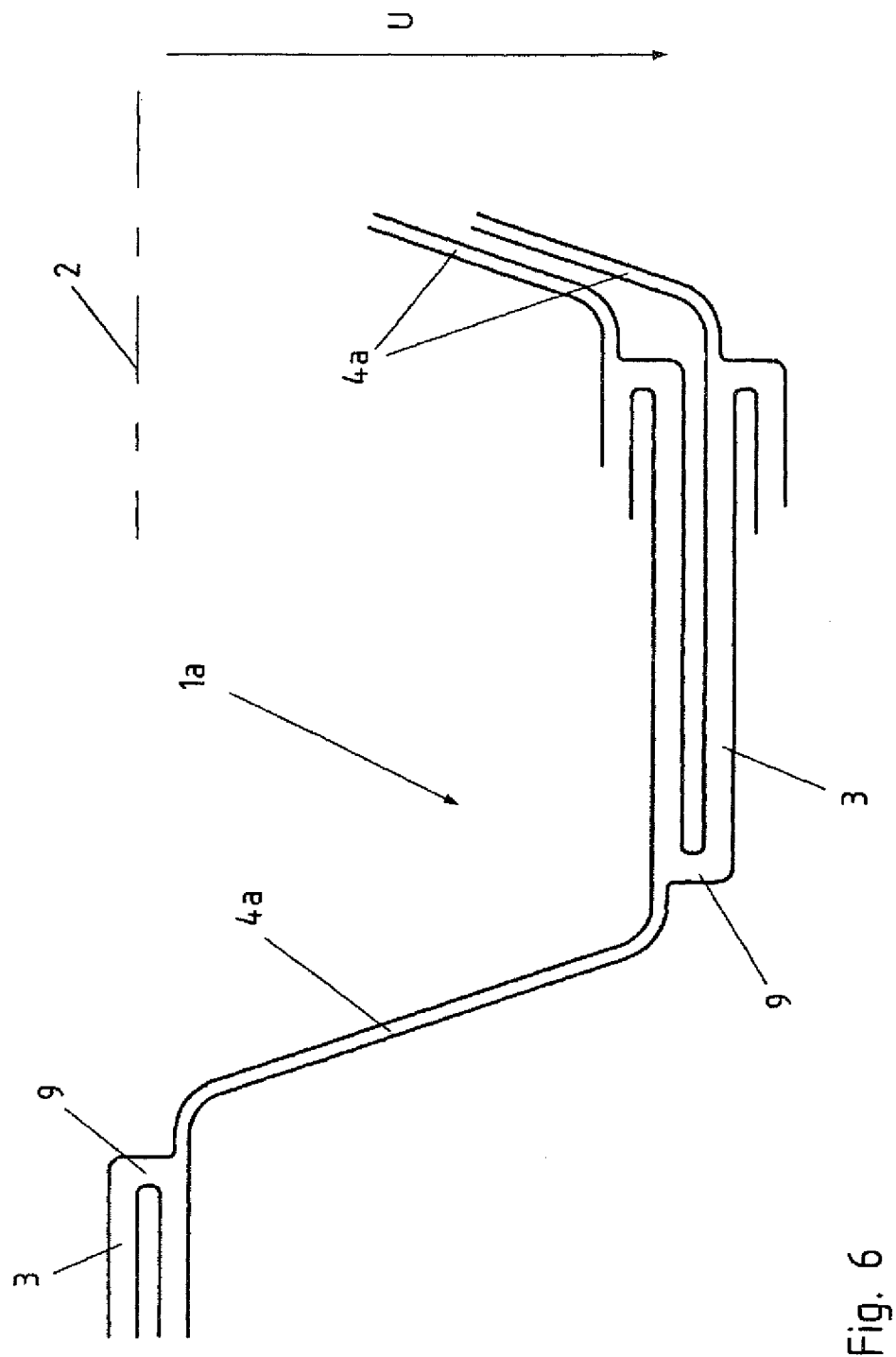
FIG. 6 a view onto a development of a connector of a second embodiment.

FIG. 6 shows a partial region of a development of a second embodiment of a stent 1a. This stent 1a has no divided connectors but only undivided connectors 4a. These also extend S-shaped.

The serpentine elements 3 are substantially identical. The connectors 4a are, however, not arranged in the apex of the arcs 9 but are rather attached to a corner of the arcs 9 and therefore quasi form an extension of a longitudinal side of a serpentine element 3. The connectors 4a are substantially straight in their further extent. They form an angle with the circumferential direction U and also with the longitudinal axis 2.

A further difference to the first embodiment is that the connectors 4a on the right hand side in the image plane do not point downwards but upwards. This means that the connectors 4a are oriented in opposite directions.

Figure 7:
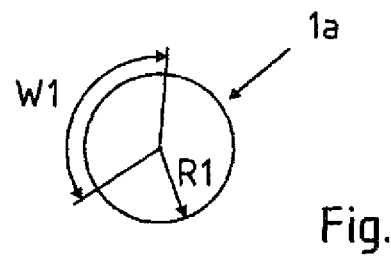
FIG. 7 a front view of the stent of FIG. 7 in the expanded state.

FIG. 7 shows a purely schematic cross sectional view of the stent 1a in the non-expanded state. The radius R1 is for example 2.5 mm. The connectors 4a extend over an angle W1 from 120° to 130°. Their curvature K1 is the reciprocal of the radius R1 (K1=1/R1).

Figure 8:
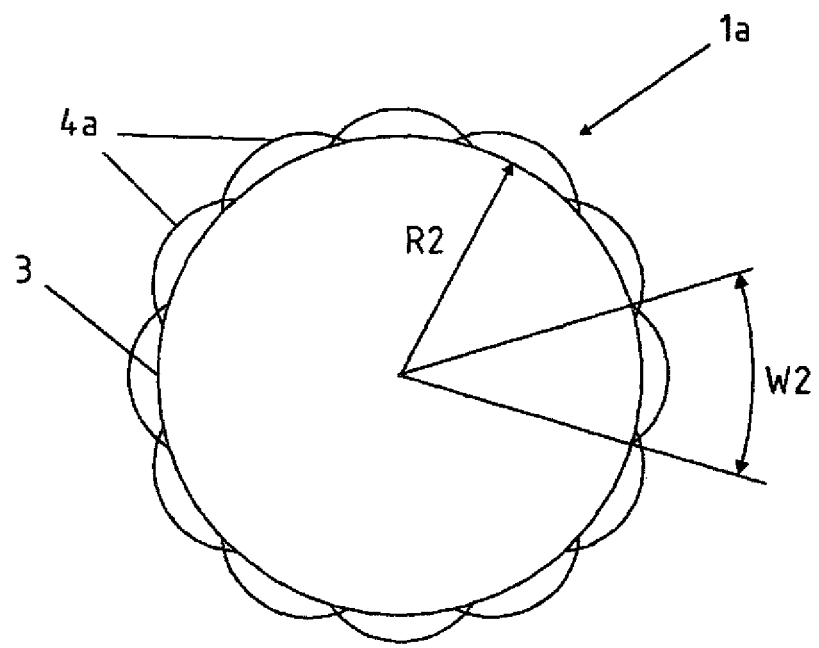
FIG. 8 a front view through the stent of FIG. 7 in the non-expanded state.
Figure 9:
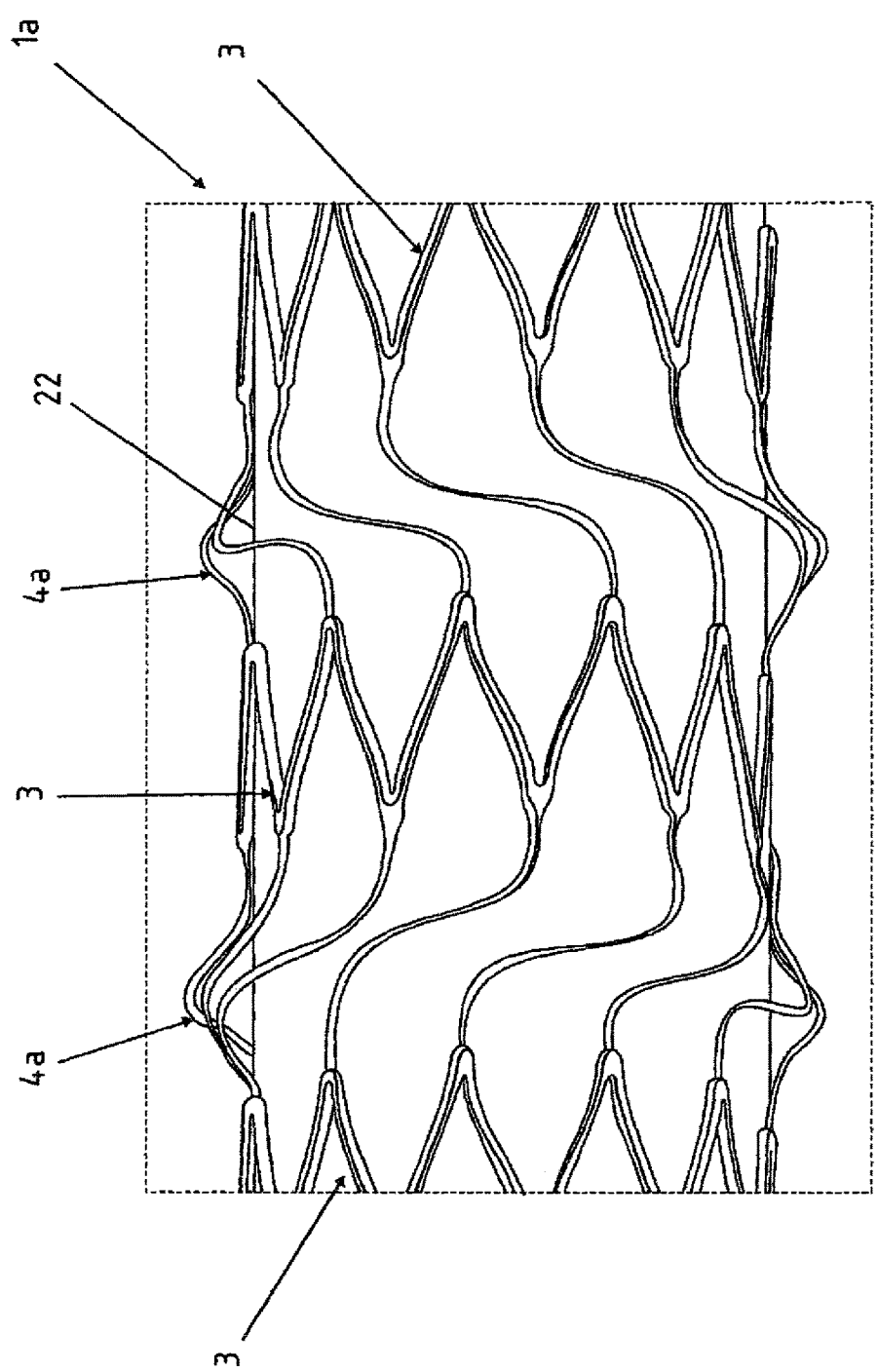
FIG. 9 a side view onto the stent of the second embodiment in the expanded state.

FIG. 8 shows the stent 1a of FIG. 7 in the expanded state, also purely schematically. The radius has slightly increased by the factor 4 and is now referred to as R2. As a consequence, the curvature K2 of the cylinder sheath has decreased by about the factor 4 (K2=1/R2). The connectors 4a, however, have still retained their original curvature K1=1/R1 in the expanded state of the stent 1a. As a result the connectors 4a significantly protrude as individual arcs over the shown circle, over the cylinder sheath formed by the serpentine elements 3. Hereby the connectors 4a slightly overlap each other in circumferential direction. This results in a circumferentially extending bulge. Each connector 4a hereby covers a much smaller angle W2, which in this exemplary embodiment is about 30°, so that 12 connectors 4a are required to form the entire bulge. FIG. 9 shows a schematic three-dimensional representation of the bulge as it is formed by the connectors 4a. For better illustration the rear part of the stent 1a is covered by a cylinder 22 located in the stent 1a. Also this embodiment can be provided with end sections 5 as in FIG. 3. The difference between the variants only lies in the design of the connectors 4a.

Figure 10:
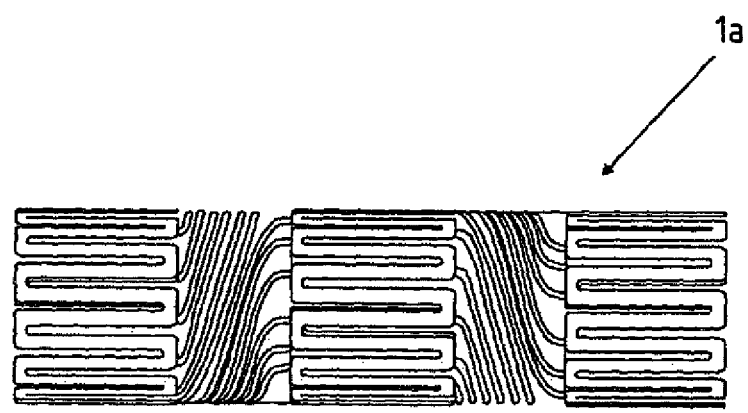
FIG. 10 a side view onto the stent of the second embodiment in the non-expanded state and FIG. 11 a view onto a development of the sheath surface of a non-expanded stent in a third embodiment.

FIG. 10 again shows a side view of the stent 1a with one-piece connectors 4a in the non-expanded state.

FIG. 11 shows the development of a stent 1b. The connectors 4b are again undivided. The difference compared to the embodiment of FIG. 6 is that the connectors 4b are not fastened on the outer sides of the arcs 9 but on the inside of the arcs 9a. For this the connectors extend as far as into the region covered by the serpentine elements 3a. They extend within the serpentine elements 3a between and parallel to the legs 23 of the serpentine elements 3a. The legs 23 are defined as the regions between the arcs 9, 9a of the serpentine elements 3a. The legs 23 in this exemplary embodiment are slightly waved so that the connectors 4b and the legs 23 extend parallel to each other.

A further difference is that the connectors 4b are not fastened on every possible arc 9, 9a, 9b but only on the inside of every third arc 9a. For this the arcs 9a are slightly wider as viewed in circumferential direction U.

A further difference is that this design of the connectors 4b is not repeated multiple times over the length of the stent 1b. It can be seen that a further type of arc 9b is present, i.e., on the side of the serpentine elements 3a that faces away from the connectors 4b. This type of arc 9b is connected on its outside with a not further shown arm of a further connector. This can be a divided or undivided connector. This is also the case for the left hand side in the image plane. This means that there is a recurring sequence of three different arcs 9, 9a, 9b, i.e., the simple arc 9 without adjoining connector, an arc 9a with a connector 4b which adjoins on the inside and an arc 9b with a connector that adjoins on the outside, wherein the connector connected thereto can for example have the design as shown in FIG. 9.

What is claimed is:

1. A stent in the form of a substantially tubular body, comprising:
   multiple serpentine, annularly expandable elements, said serpentine elements having first and second ends facing in an axial direction of the stent, said first and second ends having arcs; and
   Y-shaped connectors connecting at least three axially adjacent ones of the serpentine elements, each of said connectors having a single base arm and two fork arms having a forking point exclusively connected to the single base arm, said single base arm being connected to one of the arcs of the second end of one of the adjacent serpentine elements, said two fork arms being connected to two neighboring ones of the arcs of the first end of another one of the adjacent serpentine elements in one to one correspondence,
   wherein in a non-expanded state of the stent the connectors extend in a circumferential direction of the stent and have a curvature in the circumferential direction, said curvature in an expanded state of the stent having a size in the circumferential direction so that at least a portion of the base arm and a portion of the fork arms of the connectors protrude radially outwardly over a circumference of each of the serpentine elements.

2. The stent of claim 1, wherein in the non-expanded state of the stent, the connectors extend over an angle in a range of 120° to 240°.

3. The stent of claim 1, wherein in the expanded state of the stent a respective one of the connectors extends over an angle in a range from 30° to 85°.

4. The stent of claim 1, wherein axially adjacent ones of the connectors extend in opposite orientations.

5. The stent of claim 1, wherein all arcs of one of the serpentine elements are connected with the arcs of a neighboring one of the serpentine elements via the connectors.

6. The stent of claim 1, wherein when viewed in a development plane of the stent, the base arm is curved, so that the one of the arcs of the second end of the one of the adjacent serpentine elements is located in a different circumferential section than the neighboring arcs of the first end of the another one of the adjacent serpentine elements with which the two fork arms are connected.

7. The stent of claim 1, wherein when viewed in a development plane of the stent, the two fork arms have a curved configuration, so that the forking point at which the base arm is connected with the two fork arms is located in a different circumferential section than neighboring arcs of the first end of the another one of the adjacent serpentine elements with which the two fork arms are connected.

8. The stent of claim 7, wherein the curved configuration of the two fork arms is formed by respective fork arm arcs on the two fork arms, wherein the fork arm arcs differ from each other regarding a radius of curvature when viewed in a development plane of the stent.

9. The stent of the claim 1, wherein the fork arms of a respective one of the connectors have different lengths.

10. The stent of claim 1, wherein the two fork arms have respective first length sections, said first length sections when viewed in a development plane of the stent extending parallel to each other and having different lengths.

11. The stent of claim 1, wherein the connectors, when viewed in a development plane of the stent, have an S-shaped extent from the one of the arcs of the second end of the one of the adjacent serpentine elements to the two neighboring ones of the arcs of the first end of the another one of the adjacent serpentine elements.

12. The stent of claim 1, wherein a thickness of the base arm and the two fork arms of a connector measured in a radial direction is greater than a width of the base arm and the two fork arms measured in the circumferential direction.

* * * * *